United States Patent
Kammel et al.

(10) Patent No.: US 6,812,361 B2
(45) Date of Patent: Nov. 2, 2004

(54) PROCESS FOR PREPARING ISOCYANATOORGANOSILANES

(75) Inventors: Thomas Kammel, München (DE); Rainer Winkler, München (DE); Bernd Pachaly, Mehring (DE)

(73) Assignee: Consortium fuer elektrochemische Industrie GmbH, Munich (DE)

(*) Notice: Subject to any disclaimer, the term of this patent is extended or adjusted under 35 U.S.C. 154(b) by 19 days.

(21) Appl. No.: 10/451,499
(22) PCT Filed: Oct. 31, 2001
(86) PCT No.: PCT/EP01/12659
§ 371 (c)(1), (2), (4) Date: Jun. 20, 2003
(87) PCT Pub. No.: WO02/50086
PCT Pub. Date: Jun. 27, 2002

(65) Prior Publication Data
US 2004/0049064 A1 Mar. 11, 2004

(51) Int. Cl.[7] .................................................. C07F 7/10
(52) U.S. Cl. ....................................................... 556/414
(58) Field of Search ......................................... 556/414

(56) References Cited

U.S. PATENT DOCUMENTS 6,008,396 A  12/1999  Sheridan et al.

FOREIGN PATENT DOCUMENTS

EP  0 649 850  4/1995
EP  1 010 704  6/2000

OTHER PUBLICATIONS

Derwent Abstract corresponding to EP 1 010 704 [AN 2000–424423].

*Primary Examiner*—Samuel Barts
(74) *Attorney, Agent, or Firm*—Brooks Kushman, P.C.

(57) ABSTRACT

The invention relates to a method for producing isocyanatoorganosilane of general formula (I) $R^2R^3R^4Si-R^1-N=C=O$. According to said method, gaseous carbamatoorganosilane of general formula (II) $R^2R^3R^4Si-R^1-NH-CO-OR$ (II), wherein R represents a monovalent $C_1-C_{10}$ alkyl radical, $R^1$ represents a bivalent $C_1-C_6$ hydrocarbon radical and $R^2$, $R^3$ and $R^4$ respectively represent a methyl, ethyl, n-propyl, i-propyl, methoxy, ethoxy, n-propoxy or i-propoxy radical, is heated in the presence of a heterogeneous catalyst.

10 Claims, No Drawings

PROCESS FOR PREPARING ISOCYANATOORGANOSILANES

BACKGROUND OF THE INVENTION

1. Field of the Invention

The invention relates to a process for preparing isocyanatoorganosilanes and to certain isocyanatoorganosilanes.

2. Description of the Related Art

For some time there has been great interest in an economic method for preparing isocyanatoorganosilanes in high yields and purities. These compounds are of great economic importance, since they are used, for example, industrially as adhesion promoters between organic polymers and inorganic materials. The compounds are sometimes termed coupling agents or crosslinkers.

For preparation of isocvanatoorganosilanes, processes are preferred in which starting materials pose little or no safety risk, in order to facilitate handling and procedure. In the case of the processes previously used, isocyanatoorganosilanes are prepared in relatively low amounts in expensive, low-efficiency processes.

For example, in the process described in U.S. Pat. No. 6,008,396, carbamatoorganosilanes are converted to the isocyanates in hot inert media with elimination of alcohol. However, this process. can only be operated semi-continuously, since the concentration, of impurities in the medium, even after a short time, increases in such a manner that the purity of the desired product decreases significantly.

In the case of the process described in EP-A-1010704 for preparing isocyanatoorganosilanes, carbamatoorganosilanes are thermally cleaved in the liquid phase to give the corresponding isocyanatoorganosilanes with catalysis by tin(II) chloride. A disadvantage of this process is the highly complex process for isolating and purifying the desired products, which leads to low yields. Therefore, this process has not been employed industrially to date.

The thermal cleavage of carbamatoorganosilanes in the gas phase under atmospheric or reduced pressure is disclosed by EP-A-649850. However, the yields are unsatisfactory.

SUMMARY OF THE INVENTION

The invention relates to a process for preparing isocyanatoorganosilane of the general formula 1

(1), in which gaseous carbamatoorganosilane of the general formula 2

(2), where

R is a monovalent $C_1$–$C_{10}$-alkyl radical, $R^1$ is a divalent $C_1$–$C_6$ hydrocarbon radical and $R^2$, $R^3$ and $R^4$ are in each case a methyl, ethyl, n-propyl, isopropyl, methoxy, ethoxy, n-propoxy or isopropoxy radical, is heated to 300° C. to 1000° C. in the presence of a heterogeneous catalyst. Using the inventive process, high yields and selectivities are achieved.

DETAILED DESCRIPTION OF THE EMBODIMENTS

In the process, from the carbamatoorganosilanes of the general formula 2, alcohols of the general formula ROH are eliminated, in particular methanol, ethanol, propanol, butanol, isobutanol, pentanol, hexanol, isohexanol, cyclohexanol and 2-ethylhexanol. Preference is given to methanol and ethanol, particular preference to methanol.

The spacer $R^1$ between the organosilyl group and the carbamato group can be an unbranched or branched, saturated or unsaturated $C_1$–$C_6$ hydrocarbon groups. Preference is given to alkyl radicals, in particular unbleached alkyl radicals, particular preference being given to methylene, ethylene and propylene.

$R^2$, $R^3$ and $R^4$ are preferably methyl, methoxy, ethoxy, n-propoxy or isopropoxy radicals.

Using the process, compounds of the general formula 1 can be prepared for the first time where $R^2$ and $R^3$ are methoxy, $R^4$ is methyl and $R^1$ is methylene;

$R^2$ is methoxy, $R^3$ is ethoxy, $R^4$ is methyl and $R^1$ is methylene;

$R^2$ and $R^3$ are ethoxy, $R^4$ is methoxy, and $R^1$ is methylene; or $R^2$ and $R^3$ are methoxy, $R^4$ is ethoxy, and $R^1$ is methylene. These compounds likewise constitute subject-matter of the invention.

The heterogeneous catalysts are preferably selected from compounds of Sn(I), SN(II), Pb(II), Zn(II), Cu(I), Cu(II), Co(I), Co(II), Mg, Ca, Ba, Cr, Mo, Ti, V, W, Ce, Ni, P, Si, Al and mixed compounds thereof, and metals Pd, Pt, Co, Rh, Cu, Ag, Au, Zn, Cr, Mo, W, Cd and mixtures and alloys thereof. Catalytically active compounds are, in particular, metal salts, for example acetates, oxalates, carbonates, or sulfates. Preference is given to oxides of molybdenum, vanadium, tungsten and phosphorous, and also silicon oxides, mixtures thereof, or mixed oxides thereof, for example $Ti_2O$, $Al_2O_3$, BaO, CaO, MgO, $CeO_2$, $Cr_2O_3$, ZnO, $V_2O_4$, NiO, CuO, $Co_3O_4$, and $Fe(MoO_4)_3$. Furthermore, aluminosilicates are useful, in particular zeolites, in varying pore sizes. Metal salts in the form of hydroxides, nitrates, tartrates, citrates, heteropolyacids and modified carbon, for example graphite, transition metal nitrides, and transition metal carbides can also be used.

These metals, metal compounds or mixtures thereof are preferably applied to support materials, for example to glass wool, quartz wool, ceramics, oxidic compositions, such as $SiO_2$, $Al_2O_3$, or steatite. Support materials which can preferably be used are bodies in the form of spheres (customarily d=3–20 mm), rings (customarily $d_{outer}$ outer×h×$d_{inner}$=3–9 mm×3–9 mm×1–7 mm), monoliths (those which are customary are, for example, 1≈5–20 cm, d≈1–5 cm), cylinders (customarily d=3–20 mm), trilobes or pills.

The process is preferably carried out in a heated tubular reactor, in a coiled reactor or in a tube-bundle reactor. Customary materials, for example quartz glass or metals, can be used to produce these apparatuses.

The gaseous carbamatoorganosilane of the general formula 2 is preferably catalytically converted in a temperature range of 300–600° C., and in particular in a range of 400–500° C.

The process can be carried out with or without carrier gas, for example nitrogen, or noble gases, such as argon.

The process is preferably carried out in a pressure range of 0.01–100 bar, more preferably at 0.5–10 bar, in particular in a range of 0.5–1.5 bar.

The process can be carried out batchwise or, preferably, continuously.

As a result of the high product purity, the desired product can be produced at high purity (>97%) in a simple distillation step. The formation of six-membered isocyanurates, which has been observed at high thermal loads, is avoided by the present process.

What is claimed is:

1. A process for preparing isocyanatoorganosilanes of the formula 1

$$R^2R^3R^4Si—R^1—N=C=O \quad (1),$$

comprising heating gaseous carbamatoorganosilane of the formula 2

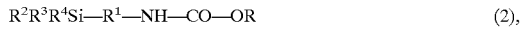

$$R^2R^3R^4Si—R^1—NH—CO—OR \quad (2),$$

where

R is a monovalent $C_1$–$C_{10}$-alkyl radical, $R^1$ is a divalent $C_1$–$C_6$ hydrocarbon radical and $R^2$, $R^3$ and $R^4$ are independently methyl, ethyl, n-propyl, isopropyl, methoxy, ethoxy, n-propoxy or isopropoxy radicals, at a temperature of 300° C. to 1000° C. in the presence of a heterogeneous catalyst.

2. The process of claim 1, wherein $R^1$ is methylene, ethylene or propylene.

3. The process of claim 1, in which $R^2$, $R^3$ and $R^4$ are methyl, methoxy or ethoxy radicals.

4. The process of claim 1, wherein the heterogeneous catalysts comprise at least one compounds of Sn(I), Sn(II), Pb(II), Zn(II), Cu(I), Cu(II), Co(I), Co(II), Mg, Ca, Ba, Cr, Mo, Ti, V, W, Ce, Ni, P, Si, Al, a mixed compound thereof, metals Pd, Pt, Co, Rh, Cu, Ag, Au, Zn, Cr, Mo, W, Cd, or mixtures and alloys thereof.

5. The process of claim 1, wherein said heating is carried out in a pyrolysis tube, in a coiled reactor, or in a tube-bundle reactor.

6. The process of claim 1, which is carried out continuously.

7. The process of claim 1, wherein said catalyst is coated onto a support material.

8. The process of claim 1, wherein following said step of heating, a mixture comprising an isocyanatoorganosilane of formula (1) and an alcohol ROH is recovered and subjected to distillation to isolate a purified isocyanatoorganosilane.

9. The process of claim 1, wherein said carbamatoorganosilane of formula 1 is heated to from 400–500° C.

10. The process of claim 1, wherein:

$R_2$ and $R^3$ are methoxy, $R^4$ is methyl and $R^1$ is methylene;

$R^2$ is methoxy, $R^3$ is ethoxy, $R^4$ is methyl and R is methylene;

$R^2$ and $R^3$ are ethoxy, $R^4$ is methoxy and $R^1$ is methylene; or $R^2$ and $R^3$ are methoxy, $R^4$ is ethoxy, and $R^1$ is methylene.

* * * * *

UNITED STATES PATENT AND TRADEMARK OFFICE
CERTIFICATE OF CORRECTION

PATENT NO. : 6,812,361 B2
DATED : November 2, 2004
INVENTOR(S) : Thomas Kammel et al.

It is certified that error appears in the above-identified patent and that said Letters Patent is hereby corrected as shown below:

Column 4,
Line 20, delete "Ris" and insert -- $R^1$ is --.

Signed and Sealed this

Fifteenth Day of February, 2005

JON W. DUDAS
*Director of the United States Patent and Trademark Office*